(12) United States Patent
Geisberger

(10) Patent No.: US 7,511,166 B2
(45) Date of Patent: Mar. 31, 2009

(54) PROCESS FOR THE PREPARATION OF ORGANYLHYDROGENSILANES

(75) Inventor: Gilbert Geisberger, Altoetting (DE)

(73) Assignee: Wacker Chemie AG, Munich (DE)

( * ) Notice: Subject to any disclaimer, the term of this patent is extended or adjusted under 35 U.S.C. 154(b) by 535 days.

(21) Appl. No.: 11/410,484

(22) Filed: Apr. 25, 2006

(65) Prior Publication Data
US 2006/0241272 A1    Oct. 26, 2006

(30) Foreign Application Priority Data
Apr. 26, 2005    (DE) .................. 10 2005 019 252

(51) Int. Cl.
C07F 7/08    (2006.01)
(52) U.S. Cl. ................................... 556/469
(58) Field of Classification Search .............. 556/469
See application file for complete search history.

(56) References Cited

U.S. PATENT DOCUMENTS

| | | | | |
|---|---|---|---|---|
| 2,834,648 A | * | 5/1958 | Bailey et al. | 423/342 |
| 3,399,222 A | * | 8/1968 | Weyenberg | 556/469 |
| 3,793,357 A | * | 2/1974 | McIntee | 556/469 |
| 4,605,543 A | | 8/1986 | Lepage et al. | |
| 4,746,752 A | * | 5/1988 | Lepage et al. | 556/469 |
| 5,550,269 A | * | 8/1996 | Boudjouk et al. | 556/415 |
| 5,654,459 A | * | 8/1997 | Kropfgans et al. | 556/469 |
| 5,670,687 A | * | 9/1997 | Geisberger et al. | 556/469 |
| 6,534,614 B2 | * | 3/2003 | Tolentino et al. | 528/12 |
| 7,148,370 B1 | * | 12/2006 | Rubinsztajn et al. | 556/469 |

FOREIGN PATENT DOCUMENTS

| | | |
|---|---|---|
| DE | 1 264 442 | 3/1968 |
| DE | 2 132 335 | 6/1970 |
| DE | 2132335 A1 | 1/1972 |
| DE | 195 20 737 | 12/1996 |
| DE | 101 57 198 | 5/2002 |
| EP | 0 296 074 | 10/1988 |
| EP | 0 776 698 | 6/1997 |
| EP | 0776698 A | 6/1997 |
| WO | WO 99/31111 | 6/1999 |

OTHER PUBLICATIONS

Derwent Abstract corres. to DE 101 57 198 [AN2002-464563], (2002).
Derwent Abstract corres. to DE 195 20 737 [AN1997-023091], (1997).
Derwent Abstract corres. to DE 2 132 335 [AN1972-02908T], (1972).
Derwent Abstract corres. to DE 1 264 442 [AN1968-03358Q], (1968).
Derwent Abstract corres. to EP 0 776 698 [AN 1997-291087], (1997).
Derwent Abstract corres. to EP 0 286 074 [AN1988-287278], (1998).
Derwent Abstract corres. to WO 99/31111 [AN 1999-397340], (1999).
Houben-Weyl, Georg Thieme Verlag, vol. XII/1, pp. 79-90, 1963.
English Patbase Abstract corresponding to DE 2132335, (2006).

* cited by examiner

*Primary Examiner*—Porfirio Nazario Gonzalez
(74) *Attorney, Agent, or Firm*—Brooks Kushman P.C.

(57) ABSTRACT

Organylhydrogensilanes are prepared by means of a comproportionation reaction according to the equation

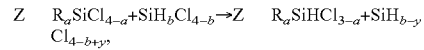

$$Z\ R_aSiCl_{4-a} + SiH_bCl_{4-b} \rightarrow Z\ R_aSiHCl_{3-a} + SiH_{b-y}Cl_{4-b+y},$$

in the presence of a catalyst which contains at least one completely organically substituted ammonium or phosphonium unit, where
R is an optionally halogen-substituted alkyl, aryl, or alkaryl radical,
a is 1, 2 or 3,
y and Z are 1, 2, 3 or 4 and
b is 2, 3 or 4.

15 Claims, No Drawings

PROCESS FOR THE PREPARATION OF ORGANYLHYDROGENSILANES

BACKGROUND OF THE INVENTION

1. Field of the Invention

The invention relates to a process for the preparation of organylhydrogensilanes via a comproportionation reaction.

2. Background Art

The demand for organylhydrogensilanes, in particular for methyldichlorosilane and dimethylchlorosilane, is substantially higher than the amount obtained as byproducts in the direct synthesis by the Müller-Rochow process.

Comproportionation reactions of organylchlorosilanes with hydrogenchlorosilanes to give organylhydrogenchlorosilanes using Lewis acids as catalysts are described in WO 99/31111. The process is not very selective, and many byproducts are formed. The preferred $AlCl_3$ catalyst is volatile and sublimes. Since inhibitors are necessary as additives, these are added during distillation.

In DE 19520737 A, the comproportionation reaction to give organylhydrogenchlorosilanes is carried out using HCl-saturated catalysts based on Zr/Al oxide. High reaction temperatures are used. This leads to the use of a large amount of energy and, owing to the lower selectivity, to more waste products.

DE 2132335 A describes the reaction of methyltrichlorosilane and dichlorosilane to give methyldichlorosilane in the presence of hydrochlorides of tertiary amines as catalysts. The catalytic activity is low and the secondary reaction of the methyldichlorosilane product with the HCl present in the catalyst to give methyltrichlorosilane and hydrogen leads to low yields.

DE 1264442 A describes comproportionation reactions of silanes with quaternary ammonium and phosphonium salts, but no specific process for the preparation of organylhydrogenchlorosilanes is disclosed.

U.S. Pat. No. 4,605,543 A describes comproportionation reactions starting from methyldichlorosilane with quaternary ammonium and phosphonium salts.

EP 776698 A describes a process in which, in a comproportionation reaction, the hydrogen is transferred to the compound whose silicon atom carries the larger number of organic substituents. The "hydrogenating agent" is methylsilane or methylchlorosilane, which is produced by disproportionation of methyldichlorosilane.

SUMMARY OF THE INVENTION

It was the object to provide an improved process for the preparation of organylhydrogensilanes. This and other objects are achieved by use of a comproportionation reaction employing an organyl chlorosilane, a chlorosilane, and a fully organyl-substituted ammonium or phosphonium compound.

DETAILED DESCRIPTION OF THE PREFERRED EMBODIMENT(S)

The invention thus relates to a process for the preparation of organylhydrogensilanes, in which a comproportionation reaction according to the equation (1)

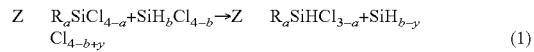

$$Z\ R_aSiCl_{4-a} + SiH_bCl_{4-b} \rightarrow Z\ R_aSiHCl_{3-a} + SiH_{b-y}Cl_{4-b+y} \quad (1)$$

is carried out in the presence of a catalyst which contains at least one completely organically substituted ammonium or phosphonium unit, where R is an optionally halogen-substituted alkyl, aryl, or alkaryl radical,
a has the values 1, 2 or 3,
y and Z have the values 1, 2, 3 or 4, and
b has the values 2, 3 or 4.

$SiH_bCl_{4-b}$ can surprisingly be used as a hydrogenating agent. In the process, no wastes form as a result of undesired secondary reactions since the catalysts selectively catalyze the H/Cl exchange. The yield is surprisingly high in view of the known processes which describe the reverse reaction, and energy costs are low since the temperature can remain low.

Examples of R are alkyl radicals such as the methyl, ethyl, n-propyl, isopropyl, n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as the cyclopentyl, cyclohexyl, cycloheptyl, and methylcyclohexyl radicals; aryl radicals such as the phenyl radical; alkaryl radicals such as the o-, m- and p-tolyl radicals, xylyl radicals and ethylphenyl radicals; and aralkyl radicals such as the benzyl radical and the α- and β-phenylethyl radicals; haloalkyl radicals such as the chloromethyl, 3-chloropropyl and 3-bromopropyl radicals; and haloaryl radicals such as the o-, m- and p-chlorophenyl radicals and the chlorotolyl radical.

The radical R preferably has 1 to 18 carbon atoms, more preferably 1 to 6 carbon atoms. In particular, the radical R is a methyl or phenyl radical.

Preferably, the comproportionation reactions (3), (4) and (5) are carried out:

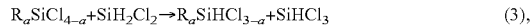
$$R_aSiCl_{4-a} + SiH_2Cl_2 \rightarrow R_aSiHCl_{3-a} + SiHCl_3 \quad (3),$$

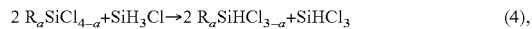
$$2\ R_aSiCl_{4-a} + SiH_3Cl \rightarrow 2\ R_aSiHCl_{3-a} + SiHCl_3 \quad (4),$$

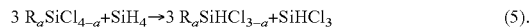
$$3\ R_aSiCl_{4-a} + SiH_4 \rightarrow 3\ R_aSiHCl_{3-a} + SiHCl_3 \quad (5).$$

The comproportionation reactions (6) and (7) are particularly preferred:

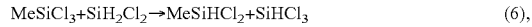
$$MeSiCl_3 + SiH_2Cl_2 \rightarrow MeSiHCl_2 + SiHCl_3 \quad (6),$$

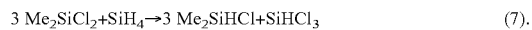
$$3\ Me_2SiCl_2 + SiH_4 \rightarrow 3\ Me_2SiHCl + SiHCl_3 \quad (7).$$

$SiH_bCl_{4-b}$ is preferably prepared in an upstream reaction, preferably in the presence of a catalyst, by disproportionation of $SiHCl_3$.

The resulting summation equation is then:

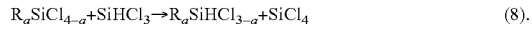
$$R_aSiCl_{4-a} + SiHCl_3 \rightarrow R_aSiHCl_{3-a} + SiCl_4 \quad (8).$$

Most preferably, $SiHCl_3$ is subjected to disproportionation in an upstream reaction and $SiH_2Cl_2$ is produced according to

$$2\ SiHCl_3 \rightarrow SiH_2Cl_2 + SiCl_4 \quad (9),$$

$SiH_3Cl$ is produced according to

$$3\ SiHCl_3 \rightarrow SiH_3Cl + 2\ SiCl_4 \quad (10),$$

or $SiH_4$ is produced according to

$$4\ SiHCl_3 \rightarrow SiH_4 + 3\ SiCl_4 \quad (11).$$

The resulting summation equations are then:

$$MeSiCl_3 + SiHCl_3 \rightarrow MeSiHCl_2 + SiCl_4 \quad (12),$$

$$Me_2SiCl_2 + SiHCl_3 \rightarrow Me_2SiHCl + SiCl_4 \quad (13).$$

In the direct reaction of the silanes $R_aSiCl_{4-a}$ with $SiHCl_3$ not by the process of the invention, the desired monohydrogenated silanes $R_aSiHCl_{3-a}$ are obtainable only in low yields: 3.4 mol % in the case of $MeSiHCl_2$, and less than 1.0 mol % in the case of $Me_2SiHCl$.

In the direct synthesis of methylchlorosilanes, addition of HCl leads to an increase in the yield of $MeSiHCl_2$ and undesired $MeSiCl_3$. With the present process, the amount of $MeSiCl_3$ obtained can be converted into $MeSiHCl_2$.

The reaction product $SiCl_4$ can be processed to give finely divided silica or can be processed in a customary conversion reaction with $H_2$ to give the starting material $SiHCl_3$ again.

The completely organically substituted ammonium or phosphonium units of the catalysts are preferably quaternary ammonium and phosphonium salts and positively charged heterocycles which have one or more completely organically substituted atoms which are selected from nitrogen and phosphorus atoms. Preferred positively charged heterocycles are imidazolium salts and pyridinium salts. The various organic substituents are hydrocarbons optionally containing heteroatom(s). Preferred heteroatoms are N, O, P, and S.

Preferably used catalysts are:

(a) quaternary ammonium salts of the general formula $R^1_4NX^1$ and (b) quaternary phosphonium salts of the general formula $R^2_4PX^2$, in which $R^1$ and $R^2$ are an optionally halogen-substituted hydrocarbon radical optionally containing heteroatoms, and $X^1$ and $X^2$ are halogen atoms.

$R^1$ and $R^2$ may be, for example, branched, straight-chain or cyclic alkyl radicals and multiple bond systems, such as aryl, alkaryl and aralkyl radicals.

Examples of $R^1$ and $R^2$ are those examples of optionally halogen-substituted alkyl, aryl or alkaryl radicals which are mentioned for R, and aralkyl radicals, such as the o-, m- and p-phenylalkyl radicals. The radicals $R^1$ and $R^2$ preferably have 1 to 18 carbon atoms, more preferably 1 to 10 carbon atoms; in particular, the radicals $R^1$ and $R^2$ are alkyl radicals having 2 to 8 carbon atoms.

The halogen atoms $X^1$ and $X^2$ are preferably chlorine, bromine or iodine, in particular chlorine.

The quaternary phosphonium salt is preferably $(n-butyl)_3(n-octyl)PCl$. The preparation of such homogenous catalysts by alkylation of tertiary phosphines with alkyl halides is described, for example, in Houben-Weyl, Georg Thieme Verlag, volume XII/1, pages 79-90, 1963.

Preferably used catalysts are furthermore:

(c) imidazolium salts of the general formula

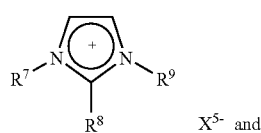

$X^{5-}$ and (d) pyridinium salts of the general formula

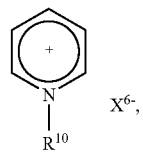

$X^{6-}$, in which $R^8$ is hydrogen or has the meaning of $R^1$ or $R^2$, $R^7$, $R^9$ and $R^{10}$ have the meaning of $R^1$ or $R^2$, and $X^5$ and $X^6$ have the meaning of $X^1$ or $X^2$. Each of these groups have their meanings independently of the others.

Preferably used catalysts are furthermore:

(e) ion exchange resins which have groups which are selected from quaternary ammonium salt groups of the general formula $R^3R^4_3NX^3$ and quaternary phosphonium salt groups of the general formula $R^5R^6_3PX^4$, which are bonded to the ion exchange resin skeleton via divalent groups $R^3$ and $R^5$, and imidazolium and pyridinium groups, in which $R^3$ and $R^5$ are divalent alkyl radicals having 1 to 20 carbon atoms, which may be interrupted by —O—, —CO— or —OCO—O— groups and $R^4$ and $R^6$ have the meanings of $R^1$ and $R^2$ and $X^3$ and $X^4$ have the meanings of $X^1$ and $X^2$.

$R^3$ and $R^5$ preferably have 3 to 10 carbon atoms.

The ion exchange resin skeleton may be any desired acid-resistant organic resin. Preferred ion exchange resin skeletons are selected from epoxy resin, polystyrene, polyvinyl chloride, polyacrylate and polyamide.

The catalysts (e) may be soluble or insoluble in the reaction medium.

Preferably used catalysts are furthermore:

(f) heterogeneous catalysts which comprise inorganic heterogeneous supports on whose surface salts are fixed quaternary ammonium salts (a), quaternary phosphonium salts (b), imidazolium salts (c) and/or pyridinium salts (d). The salts are preferably fixed physically or via coordinate bonds to the surface of the heterogeneous supports.

Preferably used catalysts are furthermore:

(g) heterogeneous catalysts which comprise inorganic heterogeneous supports on whose surface salt groups are fixed which are selected from quaternary ammonium salt groups of the above general formula $R^3R^4_3NX^3$ and quaternary phosphonium salt groups of the general formula $R^5R^6_3PX^4$, which are bound to the heterogeneous support via the divalent groups $R^3$ and $R^5$ and imidazolium and pyridinium groups which are bound to the heterogeneous support via divalent groups. The salt groups are bound to the hetergeneous support via covalent bonds.

Preferred inorganic supports are selected from zeolites, clays, porous glass, porous ceramic, silicates, porous silica such as precipitated and pyrogenic silica, porous alumina, and aluminum silicates.

The heterogeneous catalysts (f) and (g) are insoluble in the reaction medium. The heterogeneous catalysts (f) and (g) may be present in finely divided form, such as in powder form, or as moldings. The moldings may be used in the form of round panels, tubes, spheres, rods and honeycomb bodies and preferably as Raschig rings.

The preparation of heterogeneous catalysts is mentioned, for example, in EP 286074 A and EP 776698 A.

Preferably used catalysts are furthermore:
(h) ionic liquids, namely low-melting salts of quaternary ammonium, quaternary phosphonium, pyridinium and imidazolium salts. For the present process, their preferred melting points at 1 bar are not more than 150° C., preferably not more than 100° C., and most preferably not more than 50° C.

The radicals of the cations of the ionic liquids preferably correspond to the above-described radicals $R^1$ and $R^2$.

The ionic liquids are preferably used in the form of metal or transition metal halides. For example, $MX_e$ where M=Ga, Fe, Cu, Zn, In, Ti, Cd, Hg, B, Sn, Pb, Bi and X=halogen are used for the preparation of the metal or transition metal halides. However, other compositions may also be used. They may contain, for example, one or more of the following anions: $AlCl_4^-$, $Al_2Cl_7^-$, $Al_3Cl_{10}^-$, $AlEtCl_3^-$, $Al_2Et_2Cl_5^-$, $BCl_4^-$, $BF_4^-$, $BEt_3Hex^-$, $CuCl_2^-$, $Cu_2Cl_3^-$, $Cu_3Cl_4^-$, $SnCl_3^-$, $Sn_2Cl_5^-$, $PF_6^-$, $H_2PO_4^-$, $SbF_6^-$, $NO_3^-$, $HSO_4^-$, $CH_3SO_4^-$, $CF_3SO_3^-$, and $(CF_3SO_2)_2N^-$.

Specific examples of ionic liquids are:
1-ethyl-3-methylimidazolium chloride/aluminum chloride (EMIMCL/AlCl$_3$),
1-butyl-3-methylimidazolium chloride/aluminum chloride (BMIMCL/AlCl$_3$),
3-methyl-N-butylpyridinium chloride/aluminum chloride (3-MBPYCL/AlCl$_3$),
1-butylpyridium chloride/aluminum chloride (BPYCL/AlCl$_3$), and
tetra-n-butylphosphonium chloride/alumnum chloride (TBPCL/AlCl$_3$).

Imidazolium salts are particularly preferred. Suitable ionic liquids and the preparation thereof are described, for example, in DE 10157198 A. It is possible to use pure ionic liquids (h) or a mixture of ionic liquids, or mixtures of ionic liquids (h) with salts which are selected from the salts (a), (b), (c) and (d). The ionic liquids (h) can also simultaneously perform the function of a solvent or solubilizer for salts which are selected from the salts (a), (b), (c) and (d). The ionic liquids are preferably used in a proportion of from 0.1 to 80 percent by weight, in particular 1-10 percent by weight, in the reaction mixture with silanes.

The homogeneous catalysts (a), (b), (c) and (d) are soluble in the reaction medium. These catalysts are preferably used in the form of the pure substance, dissolved in a preferably high-boiling inert organic solvent, preferably a hydrocarbon, such as tetralin or decalin, or dissolved in the silane starting material $R_aSiCl_{4-a}$.

The homogeneous catalysts have the advantage that they are pumpable in the form of the pure substance or in dissolved form. As a result, the reaction procedure is simpler since the catalyst can also be metered during the ongoing process, i.e., if required, the catalyst concentration can be increased or reduced or the catalyst can be replenished or replaced by another homogeneous catalyst without down times.

In the inventive process, the phosphonium and imidazolium catalysts are distinguished by excellent thermal stability in the various organylchlorosilane media and by a high catalytic activity in the comproportionation reactions.

The process can be carried out batchwise, semicontinuously or fully continuously. It is preferably carried out fully continuously. A preferred continuous procedure is the reaction of the silane components in a reaction tube which is filled with a heterogeneous catalyst. In the case of the homogeneous catalysis, the silane starting materials are passed together with the catalyst through the reaction tube and the catalyst is then separated off by distillation and recycled.

Most preferably, the comproportionation according to the invention is carried out continuously in a bubble column. The bubble column contains either the heterogeneous or homogeneous catalyst, the silane starting materials are metered in continuously and the silanes formed are distilled off continuously. An advantage of this homogeneous catalysis process is that the catalyst does not have to be separated off subsequently and recycled.

The silane starting materials are used in gaseous or liquid form or dissolved in an inert organic solvent, in particular hydrocarbons and halohydrocarbons such as hexane, toluene, xylene or chlorobenzene.

In a preferred homogeneous procedure, the vertical, preferably thermostated reaction tube (bubble column) is filled with the catalyst, and silanes of the formulae $R_aSiCl_{4-a}$ and $SiH_bCl_{4-b}$ are preferably passed in at a pressure of from 0.1 to 20 bar, more preferably from 1 to 3 bar, preferably at a temperature of from 0 to 250° C., more preferably from 50 to 150° C. The molar ratio of starting materials $SiH_bCl_{4-b}/R_aSiCl_{4-a}$ is preferably from 0.1 to 10, preferably from 0.2 to 2.0. The catalyst concentration, based on the total amount of silanes used, is preferably from 0.1 to 80% by weight, preferably from 2 to 60% by weight, most preferably from 5 to 20% by weight.

In the preferred perparation of SiH-containing organylchlorosilanes having low boiling points, e.g. Me$_2$SiHCl or MeSiHCl$_2$, the silanes distill from the reaction tube and the reaction mixture is condensed and is then separated by fractional distillation, maintaining a substantially constant level in the reaction tube. In the case of organylchlorosilanes having higher boiling points, the reaction mixture is preferably taken off as an overflow in the upper portion of the reactor. The catalyst is thus also removed and is preferably separated from the silane mixture by distillation and recycled.

In a second preferred process variant, a heterogeneous catalyst is used in a fixed or fluidized bed, or preferably as moldings present in a theromstated tube. With the arrangement of the catalyst as moldings, the silanes of the formulae $R_aSiCl_{4-a}$ and $SiH_bCl_{4-b}$ are preferably passed in at a pressure of from 0.1 to 20 bar, more preferably from 1 to 3 bar, and at preferably a temperature of from 0 to 250° C., more preferably from 100 to 150° C. The molar ratio of starting materials $SiH_bCl_{4-b}/R_aSiCl_{4-a}$ is preferably from 0.1 to 10, more preferably from 0.2 to 2.0. The reaction mixture obtained is then preferably separated by fractional distillation.

By choosing a suitable ratio of starting materials $SiH_bCl_{4-b}/R_aSiCl_{4-a}$, the monohydrogenated silane $R_aSiHCl_{3-a}$ desired as the end product can be obtained in high yields. The compounds of the formula $R_aSiHCl_{3-a}$, in particular the SiH-containing organylchlorosilanes, are valuable starting compounds for the preparation of functional silanes or siloxanes which are obtained via a hydrosilylation reaction with organic compounds having aliphatic double or tripple bonds. A further use of dimethylchlorosilane is in the preparation of organopolysiloxanes which have dimethylhydrogensilyl groups, which are used in addition-crosslinking silicone rubber compositions.

The tetrachlorosilane obtained as a byproduct, mainly in the disproportionation of trichlorosilane, can also be commercially utilized, for example for the preparation of finely divided silica produced by flame hydrolysis. Tetrachlorosilane can also be hydrogenated with hydrogen to give trichlorosilane again, so that the cycle is closed:

The resulting overall equation is then:

$$H_2 + R_aSiCl_{4-a} \rightarrow R_aSiHCl_{3-a} + HCl$$

In all the formulae above, all symbols have their meaning independently of one another. In all formulae, the silicon atom is tetravalent.

In the context of the present invention, unless stated otherwise in each case, all stated amounts and percentages are based on weight, all temperatures are 20° C. and all pressures are 1.013 bar (abs.). All viscosities are determined at 25° C.

EXAMPLE 1

A vertical, heatable V4A steel tube having an internal diameter of 5 cm and a total length of 250 cm was filled with V4A steel Interpak 10 packings. MeOctyl$_3$NCl in the form of a 3% strength solution in MeSiCl$_3$ was used as the catalyst in the following reaction.

At a total pressure of 2.2 bar (abs.) and an internal temperature of 70° C., 1000 g/h of the MeSiCl$_3$/MeOctyl$_3$NCl solution and 650 g/h of SiH$_2$Cl$_2$ were metered continuously into the lower end of the reaction column.

At the column height of about 200 cm, the product mixture was taken off in liquid form and the composition was determined by $^1$H-NMR spectroscopy (SiCl$_4$ via GC).

| | |
|---|---|
| MeSiH$_2$Cl | 0.6 mol-% |
| MeSiHCl$_2$ | 26.6 mol-% |
| MeSiCl$_3$ | 23.5 mol-% |
| SiH$_4$ | 1.6 mol-% |
| SiH$_3$Cl | 2.4 mol-% |
| SiH$_2$Cl$_2$ | 17.1 mol-% |
| SiHCl$_3$ | 21.9 mol-% |
| SiCl$_4$ | 6.0 mol-% |

The conversion of the MeSiCl$_3$ used into MeSiHCl$_2$ was 52%. The product mixture was worked up by distillation.

EXAMPLE 2

100 g of 1-butyl-3-methylimidazolium chloride were initially introduced into a vertical, heatable V4A steel tube having an internal diameter of 5 cm and a total length of 250 cm and filled in the upper half with V4A steel Interpak 10 packings, and MeSiCl$_3$ was pumped into the reactor up to a height of fill of 150 cm. At a total pressure of 2 bar and an internal temperature of 80° C., 150 g/h of SiH$_2$Cl$_2$ and 500 g/h of MeSiCl$_3$ were metered continuously into the lower end of the reactor. The height of fill of the bubble column was kept constant by regulating the internal temperature, and the product mixture obtained at the top of the reactor was condensed and the composition determined by $^1$H-NMR spectroscopy (SiCl$_4$ via GC).

| | |
|---|---|
| MeSiH$_2$Cl | 0.1 mol-% |
| MeSiHCl$_2$ | 20.3 mol-% |
| MeSiCl$_3$ | 48.4 mol-% |
| SiH$_4$ | 0.5 mol-% |
| SiH$_3$Cl | 2.0 mol-% |
| SiH$_2$Cl$_2$ | 8.1 mol-% |
| SiHCl$_3$ | 18.2 mol-% |
| SiCl$_4$ | 2.5 mol-% |

This silane mixture was worked up by distillation. The reactor could be operated over a period of 3 months without a decrease in the catalytic activity being observable.

EXAMPLE 3

A vertical, heatable V4A steel reactor having an internal diameter of 40 cm and a total length of 500 cm was filled to a height of 200 cm with V4A Pall rings.

100 kg of Bu$_4$PCl in the form of a 30% strength mixture with MeSiCl$_3$ were additionally introduced as a catalyst into the reactor. At a total pressure of 1.9 bar and an internal temperature of 78° C., 40 kg/h of dichlorosilane mixture (composition: 94.6% of SiH$_2$Cl$_2$, 2.0% of SiHCl$_3$, 2.9% of SiH$_3$Cl; prepared by disproportionation of trichlorosilane) and 150 kg/h of MeSiCl$_3$ were continuously metered into the lower end of the reactor. The height of fill of the bubble column was kept constant by regulating the temperature, and the product mixture obtained at the top of the reactor was fed to a continuously operated distillation column. SiH$_4$, SiH$_3$Cl, MeSiH$_2$Cl and SiH$_2$Cl$_2$ were taken off in gaseous form at the top of this column and recycled to the reactor for further reaction. 190 kg/h of silane mixture in liquid form and having the following composition were taken off continously at the lower end of the column:

| | |
|---|---|
| MeSiHCl$_2$ | 25.2 mol-% |
| MeSiCl$_3$ | 46.4 mol-% |
| SiH$_2$Cl$_2$ | 1.5 mol-% |
| SiHCl$_3$ | 22.2 mol-% |
| SiCl$_4$ | 4.5 mol-% |

This silane mixture was further worked up by distillation, MeSiHCl$_2$ being obtained in more than 95% purity.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of organylhydrogensilanes, comprising comproportionating a mixture of organylhalosilanes and according to equation (1):

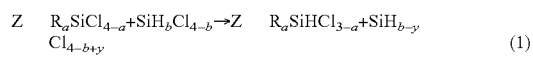

$$Z\ R_aSiCl_{4-a} + SiH_bCl_{4-b} \rightarrow Z\ R_aSiHCl_{3-a} + SiH_{b-y}Cl_{4-b+y} \quad (1)$$

in the presence of a catalyst which contains at least one completely organically substituted ammonium or phosphonium unit, where R is an optionally halogen-substituted alkyl, aryl, or alkaryl radical,
a has a value 1, 2 or 3,
y and Z have a value 1, 2, 3 or 4, and
b has a value 2, 3 or 4.

2. The process of claim 1, in which SiH$_b$Cl$_{4-b}$ is prepared in an upstream reaction, by disproportionation of SiHCl$_3$, and a resulting summation equation for the overall reaction is

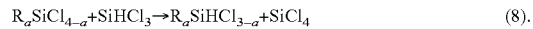

$$R_aSiCl_{4-a} + SiHCl_3 \rightarrow R_aSiHCl_{3-a} + SiCl_4 \quad (8).$$

3. The process of claim 1, in which the comproportionation reaction (3)

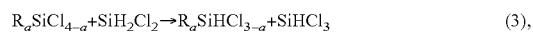

$$R_aSiCl_{4-a} + SiH_2Cl_2 \rightarrow R_aSiHCl_{3-a} + SiHCl_3 \quad (3),$$

is carried out.

4. The process of claim 2, in which the comproportionation reaction (3)

$$R_aSiCl_{4-a} + SiH_2Cl_2 \rightarrow R_aSiHCl_{3-a} + SiHCl_3 \quad (3),$$

is carried out.

5. The process of claim 1, in which the comproportionation reaction (4)

$$2\, R_aSiCl_{4-a} + SiH_2Cl_2 \rightarrow 2\, R_aSiHCl_{3-a} + SiHCl_3 \quad (4),$$

is carried out.

6. The process of claim 2, in which the comproportionation reaction (4)

$$2\, R_aSiCl_{4-a} + SiH_2Cl_2 \rightarrow 2\, R_aSiHCl_{3-a} + SiHCl_3 \quad (4),$$

is carried out.

7. The process of claim 1, in which the comproportionation reaction (5)

$$3\, R_aSiCl_{4-a} + SiH_4 \rightarrow 3\, R_aSiHCl_{3-a} + SiHCl_3 \quad (5),$$

is carried out.

8. The process of claim 2, in which the comproportionation reaction (5)

$$3\, R_aSiCl_{4-a} + SiH_4 \rightarrow 3\, R_aSiHCl_{3-a} + SiHCl_3 \quad (5),$$

is carried out.

9. The process of claim 1, in which the radical R is a methyl radical.

10. The process of claim 1, wherein the catalyst is one or more of:
(a) quaternary ammonium salts of the formula $R^1_4NX^1$,
(b) quaternary phosphonium salts of the formula $R^2_4PX^2$,
(c) imidazolium salts of the formula

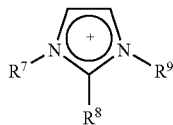

$X^{5-}$, and
(d) pyridinium salts of the formula

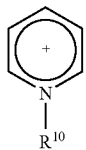

$X^{6-}$,
in which
$R^1, R^2, R^7, R^9$ and $R^{10}$ are independently, optionally halogen-substituted hydrocarbon radicals optionally one or more containing heteroatoms,
$R^8$ is hydrogen or is an optionally halogen-substituted hydrocabon radical optionally containing one or more heteroatoms, and
$X^1, X^2, X^5$ and $X^6$ are halogen atoms;
(e) ion exchange resins which have quaternary ammonium salt groups of the formula $R^3R^4_3NX^3$, quaternary phosphonium salt groups of the formula $R^5R^6_3PX^4$, bonded to the ion exchange resin skeleton via a divalent group $R^3$ or $R^5$ and imidazolium salt groups, or mixtures thereof in which $R^3$ and $R^5$ are divalent alkyl radicals having 1 to 20 carbon atoms, which may be interrupted by —O—, —CO— or —OCO—O— groups and
$R^4$ and $R^6$ have the meanings of $R^1$ and $R^2$ and
$X^3$ and $X^4$ have the meanings of $X^1$ and $X^2$;
(f) heterogeneous catalysts which comprise inorganic heterogeneous supports on whose surface quaternary ammonium salts (a), quaternary phosphonium salts (b), imidazolium salts (c), pyridinium salts (d), or mixtures thereof are fixed;
(g) heterogeneous catalysts which comprise inorganic heterogeneous supports on whose surface quaternary ammonium salt groups of the above formula $R^3R^4_3NX^3$, quaternary phosphonium salt groups of the formula $R^5R^6_3PX^4$, are bound to the heterogenous support via the divalent groups $R^3$ and $R^5$, or imidazolium and pyridinium groups bound to the heterogeneous support via divalent groups; and
(h) low-melting temperature salts of quaternary ammonium, quaternary phosphonium, pyridinium, or and imidazolium salts, or mixtures thereof.

11. The process of claim 1, in which the comproportionation is carried out continuously in a tubular reactor or in a bubble column.

12. The process of claim 10, in which the comproportionation is carried out continuously in a tubular reactor or in a bubble column.

13. The process of claim 2, wherein the catalyst is one or more of:
(a) quaternary ammonium salts of the formula $R^1_4NX^1$,
(b) quaternary phosphonium salts of the formula $R^2_4PX^2$,
(c) imidazolium salts of the formula

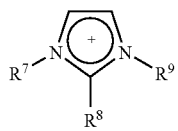

$X^{5-}$, and
(d) pyridinium salts of the formula

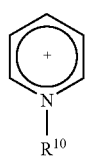

$X^{6-}$,
in which
$R^1, R^2, R^7, R^9$ and $R^{10}$ are independently, optionally halogen-substituted hydrocarbon radicals optionally one or more containing heteroatoms,
$R^8$ is hydrogen or is an optionally halogen-substituted hydrocabon radical optionally containing one or more heteroatoms, and
$X^1, X^2, X^5$ and $X^6$ are halogen atoms;
(e) ion exchange resins which have quaternary ammonium salt groups of the formula $R^3R^4_3NX^3$, quaternary phosphonium salt groups of the formula $R^5R^6_3PX^4$, bonded to the ion exchange resin skeleton via a divalent group $R^3$ or $R^5$, and imidazolium salt groups, or mixtures thereof in which $R^3$ and $R^5$ are divalent alkyl radicals having 1 to 20 carbon atoms, which may be interrupted by —O—, —CO— or —OCO—O— groups and $R^4$ and $R^6$ have the meanings of $R^1$ and $R^2$ and $X^3$ and $X^4$ have the meanings of $X^1$ and $X^2$;

(f) heterogeneous catalysts which comprise inorganic heterogeneous supports on whose surface quaternary ammonium salts (a), quaternary phosphonium salts (b), imidazolium salts (c), pyridinium salts (d), or mixtures thereof are fixed;

(g) heterogeneous catalysts which comprise inorganic heterogeneous supports on whose surface quaternary ammonium salt groups of the above formula $R^3R^4{}_3NX^3$, quaternary phosphonium salt groups of the formula $R^5R^6{}_3PX^4$, are bound to the heterogenous support via the divalent groups $R^3$ and $R^5$, or imidazolium and pyridinium groups bound to the heterogeneous support via divalent groups; and (h) low-melting temperature salts of quaternary ammonium, quaternary phosphonium, pyridinium, and imidazolium salts, or mixtures thereof.

14. The process of claim 2, in which the comproportionation is carried out continuously in a tubular reactor or in a bubble column.

15. The process of claim 13, in which the comproportionation is carried out continuously in a tubular reactor or in a bubble column.

\* \* \* \* \*